United States Patent
Klemm

(10) Patent No.: US 8,317,394 B2
(45) Date of Patent: Nov. 27, 2012

(54) X-RAY SYSTEM HAVING A DAP MEASUREMENT CHAMBER

(75) Inventor: Ingo Klemm, Jena (DE)

(73) Assignee: Siemens Aktiengesellschaft, München (DE)

( * ) Notice: Subject to any disclaimer, the term of this patent is extended or adjusted under 35 U.S.C. 154(b) by 165 days.

(21) Appl. No.: 12/709,079

(22) Filed: Feb. 19, 2010

(65) Prior Publication Data

US 2010/0215151 A1    Aug. 26, 2010

(51) Int. Cl.
*A61B 6/08* (2006.01)
(52) U.S. Cl. .................... 378/206; 378/147; 378/108
(58) Field of Classification Search .......... 378/145–153, 378/206, 108, 204
See application file for complete search history.

(56) References Cited

U.S. PATENT DOCUMENTS

| 5,446,780 A * | 8/1995 | Aichinger et al. ............ 378/204 |
| 2004/0013237 A1 * | 1/2004 | Brown et al. ................ 378/147 |

FOREIGN PATENT DOCUMENTS

| DE | 2124035 | 11/1972 |
| DE | 2421243 | 11/1975 |
| DE | 4314897 | 11/1994 |

OTHER PUBLICATIONS

German Office Action dated Jun. 16, 2010, for corresponding German Patent Application No. DE 10 2009 007 238.1, with English translation.
Chinese Office Action dated Jul. 20, 2011 for Chinese Patent Application No. 201010105851.4, with English translation.

* cited by examiner

*Primary Examiner* — Courtney Thomas
(74) *Attorney, Agent, or Firm* — Lempia Summerfield Katz LLC

(57) ABSTRACT

An improved x-ray system having a DAP measurement chamber is provided. An x-ray system has a radiation path, which extends between an x-ray radiation source and a detector. A beam splitter is arranged in the radiation path, the beam splitter being used to inject visible light into the radiation path. The DAP measurement chamber is arranged in the radiation path between the x-ray radiation source and the beam splitter. An improved collimator having a DAP measurement chamber is also provided.

6 Claims, 1 Drawing Sheet

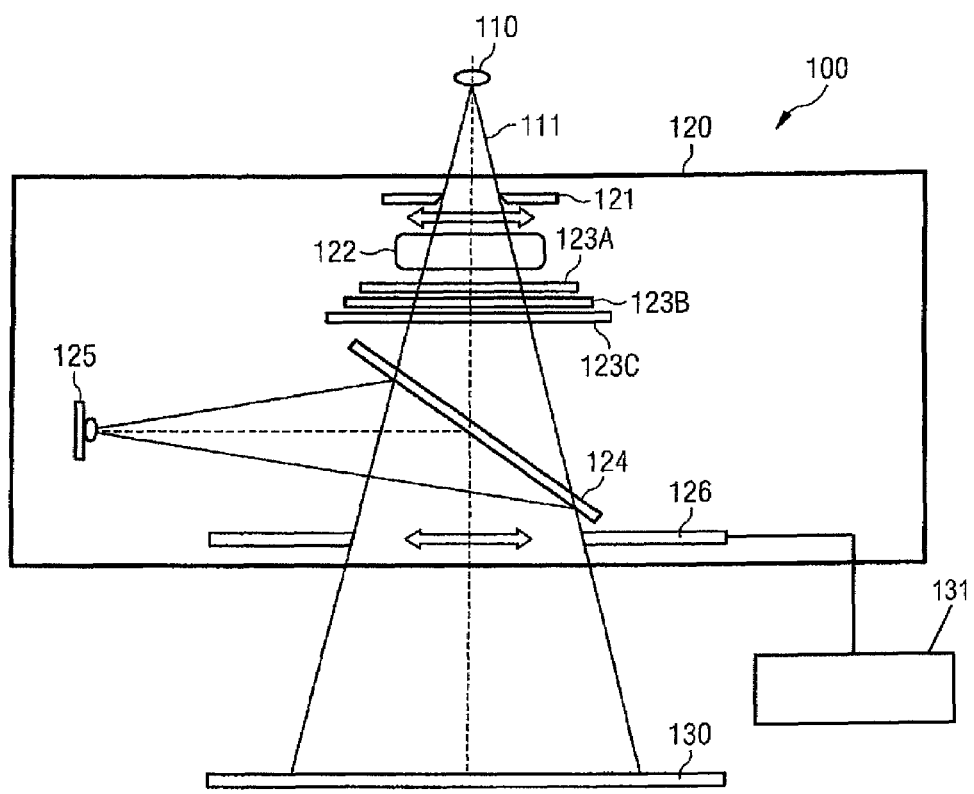

X-RAY SYSTEM HAVING A DAP MEASUREMENT CHAMBER

BACKGROUND

The present embodiments relate to an improved x-ray system and an improved collimator having a DAP measurement chamber.

Within the field of medicine, x-rays are mainly used to determine anomalies inside the body, which enable a diagnosis in conjunction with symptoms, signs and possibly other examinations. The various tissue densities in the human or animal body absorb the x-ray beams with differing strengths so that an image of the inside of the body is achieved (e.g., shading, lightening and other x-ray signs).

The problem with using x-ray radiation during therapy and diagnosis is that x-rays behave in a cancer-producing fashion. Various endeavors therefore exist for reducing the x-ray radiation, to which a patient is exposed, to the necessary level but still allowing a high quality image to be produced. Various legislative bodies stipulate the determination of the dose area product (DAP) for each x-ray procedure implemented.

In the prior art, the DAP measurement chamber is arranged in the radiation path between the collimator unit and the patient, frequently as retrofit equipment to the x-ray systems, which were installed prior to the DAP stipulations by the various legislative bodies.

If, however, the x-ray system is equipped with a device for pre-displaying the beam entry field adapted to the purpose of the examination (e.g., a light-beam localizer), the localizer light also passes through and is attenuated in the DAP measurement chamber. As a result, stronger light sources are used for the light-beam localizer, and/or certain light sources (e.g., LEDs) cannot be used since typical DAP chambers have a transmission level of 70% or less (i.e., 30% or more of the visible localizer light is absorbed).

SUMMARY AND DESCRIPTION

The present embodiments may obviate one or more of the drawbacks or limitations inherent in the related art. For example, in one embodiment, an improved x-ray system having a DAP measurement chamber may be provided.

In one embodiment, an x-ray system includes a radiation path, which extends between an x-ray radiation source and a detector, a beam splitter, which is used to inject visible light into the radiation path, arranged in the radiation path, and a DAP measurement chamber, which is arranged in the radiation path between the x-ray radiation source and the beam splitter.

The detector may be any device that is used to detect the x-ray radiation (e.g., electronic detectors or x-ray films).

In one embodiment, an arrangement of a DAP measurement chamber in a radiation path, upstream of a beam splitter, which is used to inject visible light for a light-beam localizer, is provided such that the localizer light is not attenuated, thereby making the use of commercially available LEDs possible.

In one embodiment, the DAP chamber may be provided as a first element in a collimator following near focus disks, which are used to protect against unintentionally released radiation (e.g., filters and further screens in the path or rays).

In one embodiment, a computing unit may be provided. The computing unit determines the influence of elements arranged in the radiation path downstream of the DAP measurement chamber and accordingly corrects measurement results supplied by the DAP measurement chamber so that a calculated DAP value is determined, which corresponds to the final radiation leaving the collimator.

In the prior art, the DAP measurement chamber is frequently arranged outside the collimator, thereby requiring additional space and introducing an increased cleaning requirement. These disadvantages may be avoided using the present embodiments of the arrangement of the DAP measurement chamber inside the collimator.

The present embodiments also relate to a correspondingly configured collimator for an x-ray system.

BRIEF DESCRIPTION OF THE DRAWINGS

FIG. 1 shows one embodiment of an x-ray system with a collimator arranged in a radiation path.

DETAILED DESCRIPTION OF THE DRAWINGS

A collimator 120 includes moveable near focus disks 121, which are primarily used to protect against unintentionally released radiation and form a first element of the collimator 120 that is disposed in a radiation path 111. In one embodiment, as shown in FIG. 1, a DAP measurement chamber 122 is arranged in the radiation path 111. Filter elements 123A, 123B, 123C, which may be moved mechanically in the radiation path 111, are downstream of the DAP measurement chamber 122.

A beam splitter 124 following the filter elements 123 in the radiation path is used to inject visible light from a light source 125 into the radiation path 111 in order to realize a light-beam localizer, which is used for pre-displaying the beam entry field adapted to the purpose of the examination. A last collimator element in the radiation path 111 forms moveable screens 126, with which a boundary of the illumination field may be effected.

A computing or evaluation unit 131, with which the influence of the elements following the DAP measurement chamber 122 in the radiation path 111 (e.g., beam elements shown in the example in FIG. 1: the filters 123, the beam splitter 124, the movable screens 126) on the measurement result is taken into account, is shown in FIG. 1. The beam-modifying influence of each of the beam elements is known. The beam elements are transferred as parameters to a software running on the computing or evaluation unit 131. The influence of each beam element and, if necessary, any meaningful combination of the beam elements, is known (e.g., on account of previous measurements) and suitably stored in a storage device. The storage device is accessed by the software with the aid of the transferred parameters. The influence of each beam element is also determined with the aid of the known beam-modifying influence parameters of the relevant beam element using simulation or similar methods in a special processing act. DAP values may be calculated from actual DAP measured values, which correspond to the radiation path upstream of the beam elements, the DAP values corresponding to the final radiation leaving the collimator.

In accordance with the present embodiments, the DAP measurement chamber may also be arranged in the radiation path 111, downstream of the filter elements 123 and upstream of the beam splitter 124.

In one embodiment, an LED may be used as a light source 125, since the attenuation of the localizer light is omitted by the DAP measurement chamber.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An x-ray system comprising:
   an x-ray path that extends between an x-ray radiation source and a detector;
   a beam splitter operable to inject visible light into the x-ray path, the beam splitter being arranged in the x-ray path;
   a DAP measurement chamber that is arranged in the x-ray path between the x-ray radiation source and the beam splitter;
   near focus disks operable to protect against unintentionally released radiation, the near focus disks being arranged in the x-ray path; and
   a filter arranged in the x-ray path,
   wherein the DAP measurement chamber is arranged in the x-ray path between the near focus disks and the filter.

2. The x-ray system as claimed in claim 1, further comprising a computing unit configured to determine an influence of the beam splitter arranged downstream of the DAP measurement chamber in the x-ray path and correspondingly correct measurement results supplied by the DAP measurement chamber.

3. The x-ray system as claimed in claim 1, further comprising a movable screen arranged in the x-ray path between the beam splitter and the detector.

4. The x-ray system as claimed in claim 3, further comprising a computing unit configured to determine an influence of the beam splitter arranged downstream of the DAP measurement chamber in the x-ray path and correspondingly correct measurement results supplied by the DAP measurement chamber.

5. A collimator for an x-ray system, the collimator being arranged in a radiation path of the x-ray system and comprising:
   a beam splitter operable to inject visible light into the radiation path;
   a DAP measurement chamber that is arranged in the radiation path between a radiation entry opening of the collimator and the beam splitter;
   near focus disks operable to protect against unintentionally released radiation; and
   a filter,
   wherein the DAP measurement chamber is arranged in the radiation path between the near focus disks and the filter.

6. An x-ray system comprising:
   an x-ray path that extends between an x-ray radiation source and a detector;
   a beam splitter operable to inject visible light into the x-ray path, the beam splitter being arranged in the x-ray path;
   a DAP measurement chamber that is arranged in the x-ray path between the x-ray radiation source and the beam splitter; and
   a computing unit configured to determine an influence of the beam splitter arranged downstream of the DAP measurement chamber in the x-ray path and correspondingly correct measurement results supplied by the DAP measurement chamber.

* * * * *